(12) United States Patent
Boiadjiev et al.

(10) Patent No.: US 7,579,052 B2
(45) Date of Patent: Aug. 25, 2009

(54) METHOD OF MAKING GOLD THIOLATE AND PHOTOCHEMICALLY FUNCTIONALIZED MICROCANTILEVERS

(75) Inventors: Vassil I. Boiadjiev, Knoxville, TN (US); Gilbert M. Brown, Knoxville, TN (US); Lal A. Pinnaduwage, Knoxville, TN (US); Thomas G. Thundat, Knoxville, TN (US); Peter V. Bonnesen, Knoxville, TN (US); Gudrun Goretzki, Nottingham (GB)

(73) Assignee: UT-Battelle, LLC, Oak Ridge, TN (US)

( * ) Notice: Subject to any disclaimer, the term of this patent is extended or adjusted under 35 U.S.C. 154(b) by 0 days.

(21) Appl. No.: 11/859,047

(22) Filed: Sep. 21, 2007

(65) Prior Publication Data
US 2008/0085379 A1     Apr. 10, 2008

Related U.S. Application Data

(62) Division of application No. 11/152,627, filed on Jun. 14, 2005, now abandoned.

(60) Provisional application No. 60/609,610, filed on Sep. 14, 2004.

(51) Int. Cl.
*B05D 3/10* (2006.01)
*B05D 3/12* (2006.01)
*G01N 7/00* (2006.01)

(52) U.S. Cl. ........................ 427/595; 73/23.2; 73/24.01; 73/24.06; 73/64.53; 427/299; 427/327; 427/337

(58) Field of Classification Search .................. 427/595, 427/299, 327
See application file for complete search history.

(56) References Cited

U.S. PATENT DOCUMENTS 5,270,163 A    12/1993  Gold et al.
5,485,096 A     1/1996  Aksu
(Continued)

FOREIGN PATENT DOCUMENTS

JP       02003166990 A     6/2003
(Continued)

OTHER PUBLICATIONS

Pinnaduwage, L.A. et al."Sensitive Detection of Plastic Explosives with Self-Assembled Monolayer-Coated Microcantilevers." Applied Physics Letters, vol. 83, No. 7 (Aug. 18, 2003), pp. 1471-1473.*

(Continued)

*Primary Examiner*—Michael Kornakov
*Assistant Examiner*—Alexander Weddle
(74) *Attorney, Agent, or Firm*—Boyle Fredrickson, S.C.

(57) ABSTRACT

Highly sensitive sensor platforms for the detection of specific reagents, such as chromate, gasoline and biological species, using microcantilevers and other microelectromechanical systems (MEMS) whose surfaces have been modified with photochemically attached organic monolayers, such as self-assembled monolayers (SAM), or gold-thiol surface linkage are taught. The microcantilever sensors use photochemical hydrosilylation to modify silicon surfaces and gold-thiol chemistry to modify metallic surfaces thereby enabling individual microcantilevers in multicantilever array chips to be modified separately. Terminal vinyl substituted hydrocarbons with a variety of molecular recognition sites can be attached to the surface of silicon via the photochemical hydrosilylation process. By focusing the activating UV light sequentially on selected silicon or silicon nitride hydrogen terminated surfaces and soaking or spotting selected metallic surfaces with organic thiols, sulfides, or disulfides, the microcantilevers are functionalized. The device and photochemical method are intended to be integrated into systems for detecting specific agents including chromate groundwater contamination, gasoline, and biological species.

7 Claims, 7 Drawing Sheets

U.S. PATENT DOCUMENTS

| | | | |
|---|---|---|---|
| 6,575,020 | B1 | 6/2003 | DeCharmoy Grey et al. |
| 6,617,040 | B2 | 9/2003 | Houser et al. |
| 2003/0010097 | A1 | 1/2003 | Porter et al. |
| 2003/0222232 | A1 | 12/2003 | Welland et al. |
| 2004/0152211 | A1 | 8/2004 | Majumdar et al. |

FOREIGN PATENT DOCUMENTS

| | | | |
|---|---|---|---|
| WO | WO02/19407 | * | 7/2002 |
| WO | 03/044530 | | 5/2003 |
| WO | 03/062135 | | 7/2003 |
| WO | 03/067248 | | 8/2003 |
| WO | 03/071258 | | 8/2003 |
| WO | 03/104784 | | 12/2003 |
| WO | 2004/059306 | | 7/2004 |
| WO | 2007011376 | | 1/2007 |

OTHER PUBLICATIONS

Turyan, Iva et al. "Selective Determination of Cr(VI) by a Self-Assembled Monolayer-Based Electrode." Anal. Chem., vol. 69 (1997), pp. 894-897.*

Hai-Feng, Ji et al. "Ultrasensitive Detection of CrO4 2- Using a Microcantilever Sensor." Anal. Chem., vol. 73 (2001), pp. 1572-1576.*

European Patent Office, PCT/US2005/032877, "International Search Report," Feb. 1, 2007.

Andreas Hierlemann and Henry Baltes, "CMOS-Based Chemical Microsensors," The Royal Society of Chemistry Journal, 2003, pp. 15-28, vol. 128.

Min Yue, et al., "A 2-D Microcantilever Array for Multiplexed Biomolecular Analysis," Jornal of Microelectromechanical Systems, 2004, pp. 290-299, vol. 13, No. 2.

M. Alvarez, et al., "Nanomechanics for Specific Biological Detection," Proceedings of SPIE, 2003, pp. 197-206, vol. 5118.

Iva Turyan and Daniel Mandler, "Selective Determination of CR(VI) by a Self-Assembled Monolayer-Based Electrode," Anal. Chem., 1997, pp. 894-897, vol. 69.

F. Tian, et al., "Selective Detection of CR(VI) Using a Microcantilever Electrode Coated with a Self-Assembled Monolayer," J. Vac. Sci, Technol. A, 2005, pp. 1022-1028, vol. 23, No. 4.

Robert L. Gunter, et al., Investigation of DNA Sensing Using Piezoresistive Microcantilever Probes, IEEE Sensors Journal, 2004, pp. 430-433, vol. 4, No. 4.

J. Terry, et al., "Determination of the Bonding of Alkyl Monolayers to the Si(111) Surface Using Chemical-Shift ...," Appl Phys Lett, 1997, pp. 1056-1058, vol. 71, Issue 8.

J. Terry, et al., "Reactivity of the H-Si (111) Surface," Nucl Instrum Methods Phys Res, Sect B, 1997, pp. 94, vol. 133.

J. Terry, et al., "Alkyl-Terminated Si(111) Surfaces: A High-Resolution, Core Level Photoelectron Spectroscopy Study," J of Appl Phys, 1999, pp. 213-221, vol. 85, No. 1.

R.L. Cicero, et al., Photoreactivity of Unsaturated Compounds with Hydrogen-Terminated Silicon(111), Langmuir, 2000, pp. 5688-5695, vol. 16.

L.A. Pinnaduwage, et al., "Detection of Hexavalent Chromium in Ground Water Using a Single Microcantilever Sensor," Sensor Letters, pp. 1-6, vol. 2, Issue 1-6.

V.I. Boiadjieve, et al., "Photochemical Hydrosilylation," Langmuir, 2005.

X. Zhou, et al., "Roles of Charge Polarization and Steric Hindrance in Determining the Chemical Reactivity of Surface Si-H ...," J Phys Chem B, 2001, pp. 156-163, vol. 105.

A. Arafat, et al., "Tailor-Made Functionalization of Silicon Nitride Surfaces," J Am Chem Soc, 2004, pp. 860-8601, vol. 126.

R. Voicu, et al., "Formation, Characterization, and Chemistry of Undecanoic Acid-Terminated Silicon Surfaces ...," Langmuir, 2004, pp. 11713-11720, vol. 20.

C.M. Yam, et al., "Protein-Resistant Monolayers Prepared by Hydrosilylation ...," Chemical Communications, 2004, pp. 2510-2511.

J. M. Buriak, "Organometallic chemistry on Silicon and Germanium Surfaces," Chemical Reviews, 2002, pp. 1271-1308, vol. 102, No. 5.

I. Fleming, Comprehensive Organic Chemistry, pp. 568, vol. 3.

Mosier-Boss and Lieberman, "Surface-Enhanced Raman Spectroscopy (SERS) and Molecular Modeling of the Chromate Interaction with ..." Langmuir, 2003, pp. 6826-6836, vol. 19.

Hai-Feng, et al., "Ultrasensitive Detection of CrO42- Using a Microcantilever," 2001, Anal. Chem. pp. 1572-1576, vol. 73.

L.A. Pinnaduwage, et al., Sensitive Detection of Plastic Explosives with Self-Assembled Monolayer-Coated Microcantilevers, 2003, Applied Physical Letters, pp. 1471-1473, vol. 83, No. 7.

* cited by examiner

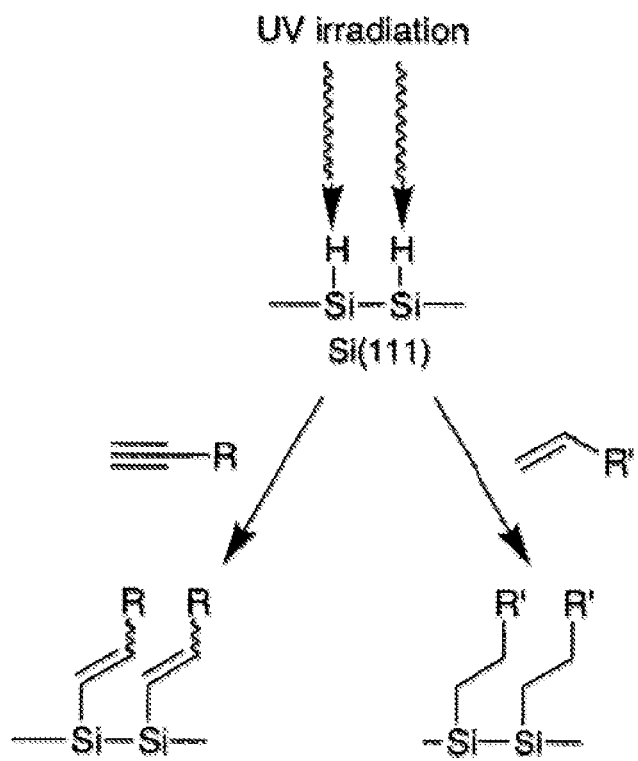
*Fig. 5 – Prior Art*
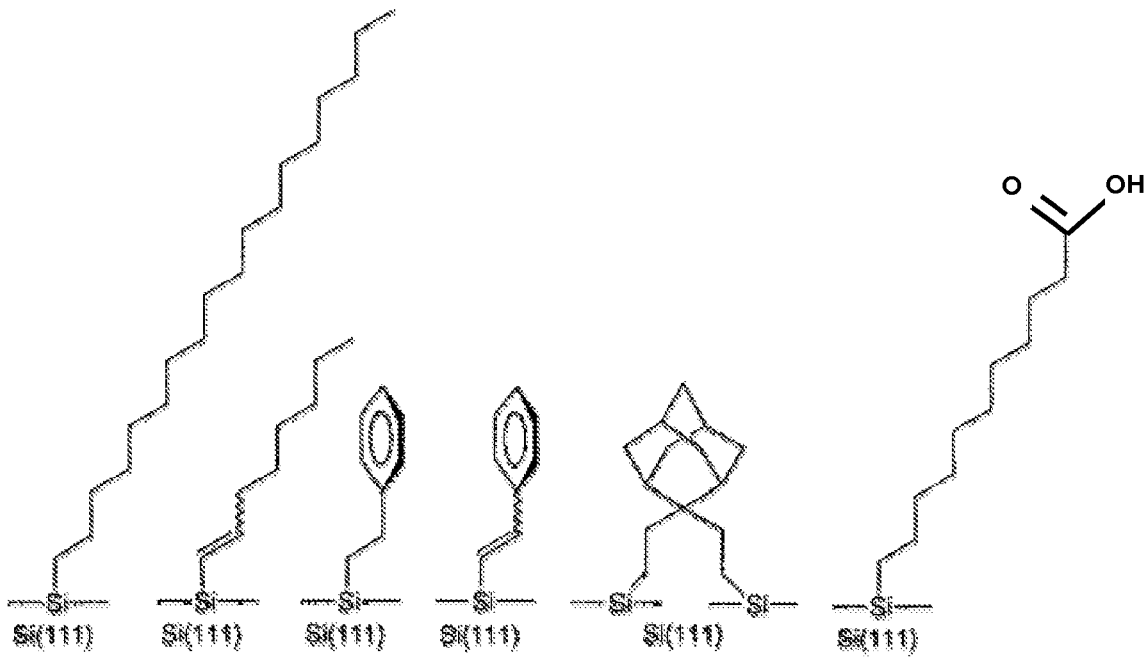
*Fig. 6 – Prior Art*

METHOD OF MAKING GOLD THIOLATE AND PHOTOCHEMICALLY FUNCTIONALIZED MICROCANTILEVERS

CROSS-REFERENCE TO RELATED APPLICATIONS

This application is a divisional of U.S. application Ser. No. 11/152,627 filed Jun. 14, 2005, which claims priority to U.S. Provisional Patent Application 60/609,610 filed Sep. 14, 2004, and is related to U.S. patent application Ser. No. 11/059,170, filed Feb. 16, 2005, all herein incorporated by reference.

STATEMENT REGARDING FEDERALLY SPONSORED RESEARCH

This invention was made with United States Government support under Contract No. DE-AC05-00OR22725 between the United States Department of Energy and U.T. Battelle, LLC. The United States Government has certain rights in this invention.

FIELD OF THE INVENTION

This invention relates to highly sensitive sensor platforms for the detection of specific reagents, such as chromate, gasoline and biological species, using microcantilevers and other microelectromechanical systems (MEMS) whose surfaces have been modified with photochemically attached organic monolayers, such as self-assembled monolayers (SAM), or gold-thiol surface linkage. The microcantilever sensors use photochemical hydrosilylation to modify silicon surfaces and gold-thiol chemistry to modify metallic surfaces thereby enabling individual microcantilevers in multicantilever array chips to be modified separately. By focusing the activating UV light sequentially on selected silicon or silicon nitride hydrogen terminated surfaces and soaking or spotting selected metallic surfaces with organic thiols, sulfides, or disulfides, the microcantilevers are functionalized. The device and photochemical method are intended to be integrated into systems for detecting specific agents including chromate groundwater contamination, gasoline, and biological species.

BACKGROUND OF THE INVENTION

Micro-electro-mechanical systems (MEMS) are likely candidates for extremely sensitive, inexpensive sensors, which can be mass produced. Microcantilever sensors offer much better sensitivities compared to other MEMS sensors and have surface areas of the order $10^{-4}$ cm$^2$, which is smaller than that of other miniature devices (such as Surface Acoustic Wave devices, SAW) by orders of magnitude. They can be mass produced at relatively low cost using standard semiconductor manufacturing processes and have demonstrated superior detection sensitivities for physical, chemical and biological sensing. Microcantilever-based sensors have been shown to be extremely sensitive; however silicon or silicon nitride microcantilevers coated on one surface with gold do not have any particular chemical selectivity. Chemical selectivity has been achieved by coating the gold surface of the microcantilevers with a selective film such as a self-assembled monolayer (SAM) of an alkane thiol having a head group suitable for molecular recognition. Also, functionalized films can be attached to hydrogen terminated silicon and silicon nitride surfaces by photochemical hydrosilylation to achieve more stable coatings. The main feature distinguishing microcantilevers from other MEMS is their unique bending response. They have a high surface-to-volume ratio, and therefore changes in the Gibbs surface free energy induced by surface-analyte interactions lead to large surface forces. When such interactions are restricted to one surface, then the resulting differential stress leads to bending of the cantilever. This bending detection mode can be used in liquid phase, as well as in gas phase, which makes cantilever sensors suitable for both molecular and ionic analytes if selective adsorption can be achieved on one of their surfaces using analyte-specific surface functionalities. A preferred approach to the design of selective sensors is to immobilize agents for selective molecular recognition in a matrix that mimics the organic medium in a solvent extraction system. In this manner, the matrix can enhance both the separation and the achievement of chemical selectivity. The transduction part of the microcantilever sensor is based on binding the molecular recognition agent to one surface of the cantilever so that the adsorption-induced stress change can be detected via bending of the microcantilever.

A problem exists with the formation of SAM coatings on gold coated cantilevers if an array of cantilevers is used. It is difficult to apply a coating, especially if a long period of time is required for a tightly packed layer to form, to a single cantilever in an array without contaminating other cantilevers in the array. Other approaches to modifying a single surface of a silicon cantilever involve reaction of silane reagents with the Si—OH groups on the surface, but again it is problematic to modify only a single cantilever in an array. The photoactivation method of this invention provides a solution to this problem wherein cantilevers are only activated to react with an ethylene substituted hydrocarbon when irradiated with UV light.

Arrays of cantilevers can be conveniently prepared with each cantilever or group of cantilevers having a separate molecular recognition agent to impart chemical selectivity. Attachment of molecular recognition agents to the surface with robust Si—C bonds gives a layer with superior stability. For example, chromium(VI) or chromate can be selectively detected by the microcantilever of this invention.

Chromium is naturally occurring in several different oxidation states. The most frequently encountered forms are the III and VI oxidation states. Chromium(III) is an essential trace element in the human body and plays an important role in the metabolism of glucose, lipids, and proteins. In contrast, Cr(VI) in the form of chromate ($CrO_4^{2-}$) is considered to be toxic to animals and humans. Most of the methods used to determine $CrO_4^{2-}$ (such as ion exchange, chromatography, and atomic absorption spectroscopy) are generally time-consuming, have less than desired accuracy, or are expensive.

In addition, Cr(VI) is more soluble in groundwater than Cr(III), and thus has a greater potential of affecting human health and the environment. Various techniques have been tested for the direct determination of Cr(VI) in water, but most techniques are not suitable due to insufficient detection limits and/or matrix interferences. The method that is widely being used at present requires selective reaction of Cr(VI) with 1,5-diphenylcarbohydrazide followed by spectrophotometry. The commercial sensor technique based on the above method and used widely for Cr(VI) monitoring, has a detection limit of $\approx 1.9 \times 10^{-7}$ M, close to the current EPA regulation level of $2.1 \times 10^{-7}$ M. However, this method is not viable for remote monitoring, and also would not be applicable if federal/local regulated levels are tightened. Therefore, developing inexpensive, easily deployable techniques with higher sensitivity is important for environmental monitoring and remediation. Due to the possibility of mass deployment at low cost, microelectromechanical systems (MEMS), especially microcantilevers, have attracted attention recently due to their high sensitivity of detection.

BRIEF DESCRIPTION OF THE INVENTION

Photochemical hydrosilylation of 11-undecenyltriethylammonium bromide with hydrogen-terminated silicon microcantilever surfaces yielded a robust quaternary ammonium terminated organic monolayer that is suitable for chromate detection. Terminal vinyl substituted hydrocarbons with a variety of molecular recognition sites can be attached to the surface of silicon via the photochemical hydrosilylation process. Since the chemicals only react at the surface of Si when irradiated it allows an array of cantilevers to be sequentially modified by exposing an array to the derivatization agent but only activating one or a select group of cantilevers before changing the solution and activating a different cantilever of group of cantilevers. Another embodiment of this invention enables the detection of hexavalent chromium, Cr(VI), in ground water using at least one microcantilever coated with a self-assembled monolayer of 4-mercaptopyridine. The microcantilever sensors use gold-thiol attachment approach for 4-mercaptopyridine (4-MPy) and photochemical hydrosilylation for grafting 11-undecenyltriethylammonium bromide or vinyl pyridine to modify the microcantilever surface for chromate sensing.

One embodiment of the device and method enables the detection of hexavalent chromium, Cr(VI), in ground water using a single microcantilever sensor coated with a self-assembled monolayer of 4-mercaptopyridine. The experiments showed that $CrO_4^{2-}$ ions can be detected with the microcantilever sensor in the presence of significant concentrations (>1000 µg/l) of $Ca^{2+}$, $Cl^-$, $Mg^{2+}$, $NO_3^-$, $K^+$, $Na^+$, and $SO_4^{2-}$ ions and a variety of other ions of smaller concentrations. The chromate concentrations were also measured using the Hach spectrophotometric kit, which is widely used for chromate monitoring. The cantilever measurements are an order of magnitude more sensitive compared to the spectrophotometric method currently in use, and are amenable for remote detection.

The microcantilever sensor uses gold-thiol or photochemical hydrosilylation to modify the microcantilever surface. The photochemical process enables individual microcantilevers in multicantilever array chips to be modified separately by focusing the activating UV light sequentially on each particular cantilever. Grafting of selected gold coated microcantilevers can be achieved by spotting techniques. The surface functionalities retain their affinity toward Cr(VI), and the organic monolayer is dense enough to generate significant surface stress upon subsequent adsorption of chromate ions from aqueous solutions.

BRIEF DESCRIPTION OF THE DRAWINGS

FIG. 5 shows photochemical hydrosilylation of alkenes and alkynes. Figure taken from Buriak, Chem. Rev. 2002, 102 (5), 1271-1308.

FIG. 6 shows surface structures reported by Buriak, Chem. Rev. 2002, 102 (5), 1271-1308 and Voicu, R., *Langmuir*, 2004, 20, pp. 11713-11720.

DETAILED DESCRIPTION OF THE INVENTION

Chromate cantilever sensors using two different types of chromate-specific surface functionalities bound to gold-coated cantilever surfaces as thiol-based pyridine and thiol-based quaternary ammonium terminated self-assembled monolayers (SAMs) are described. The 4-mercaptopyridine based microcantilever chromate sensor has exceptional stability and very high selectivity and can be used for months in acidic media utilizing a single cantilever. The 12-mercaptododecyltriethylammonium bromide based chromate sensor, despite its superior initial sensitivity to chromate, appeared to be unstable and lost its activity within 1 week. Ethanol solutions of the quaternary ammonium terminated thiol (~1 mM) from the self-assembly process were studied 2 weeks after the cantilever treatment and indicated significant degradation of the quaternary ammonium thiol. Some decomposition was also detected in the solid compound, which was stored in a closed container for a similar time period. We hypothesize that nucleophilic attack of the sulfur on the carbon attached directly to the positive nitrogen analogous to Hofmann degradation may have occurred.

Figure 4:
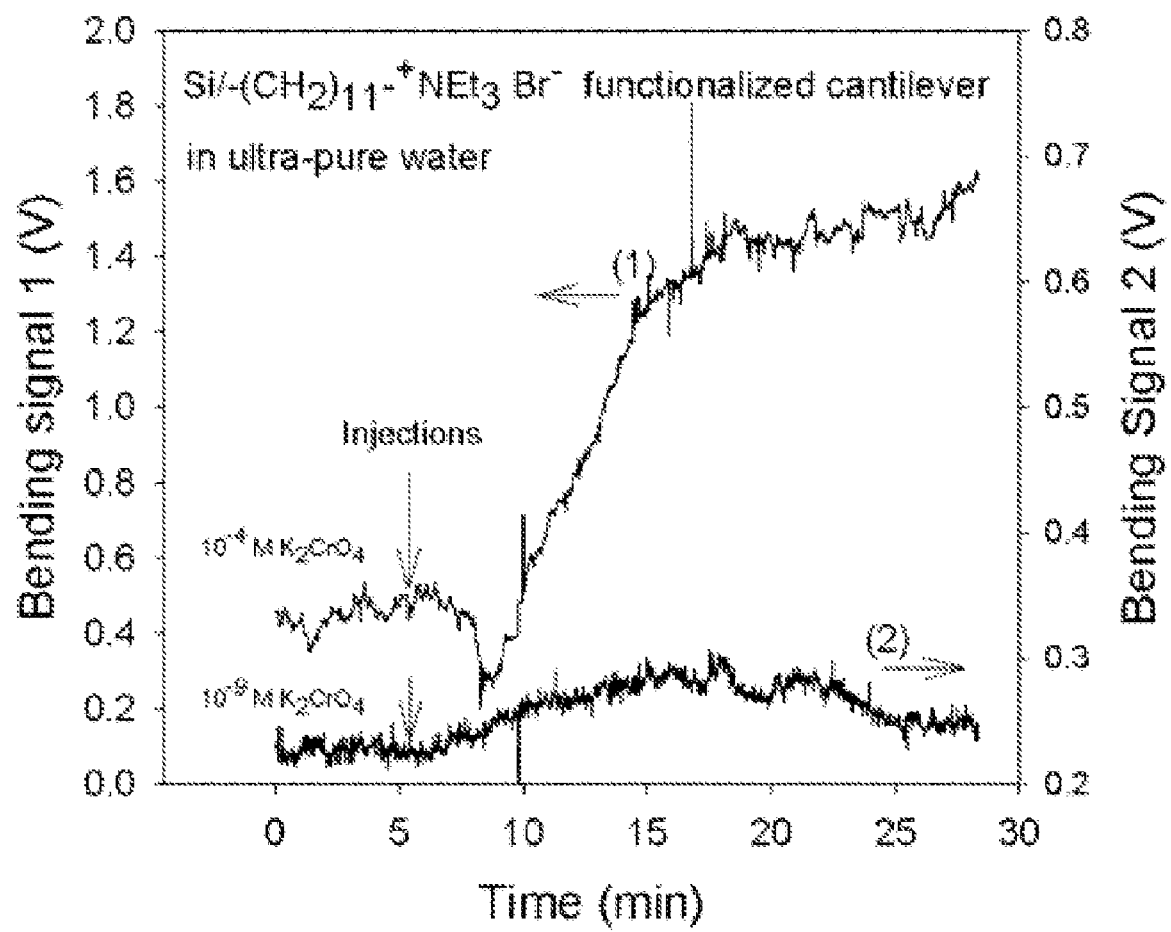
FIG. 4 is the bending response of a gold-coated silicon microcantilever, modified with 11-undecenyltriethylammonium bromide by photochemical hydrosilylation on the silicon side, upon injections of 1 mL of sample chromate solutions: (1) $1 \times 10^{-4}$ M $CrO_4^{2-}$, left scale; (2) $1 \times 10^{-9}$ M $CrO_4^{2-}$, right scale.
Figure 8:
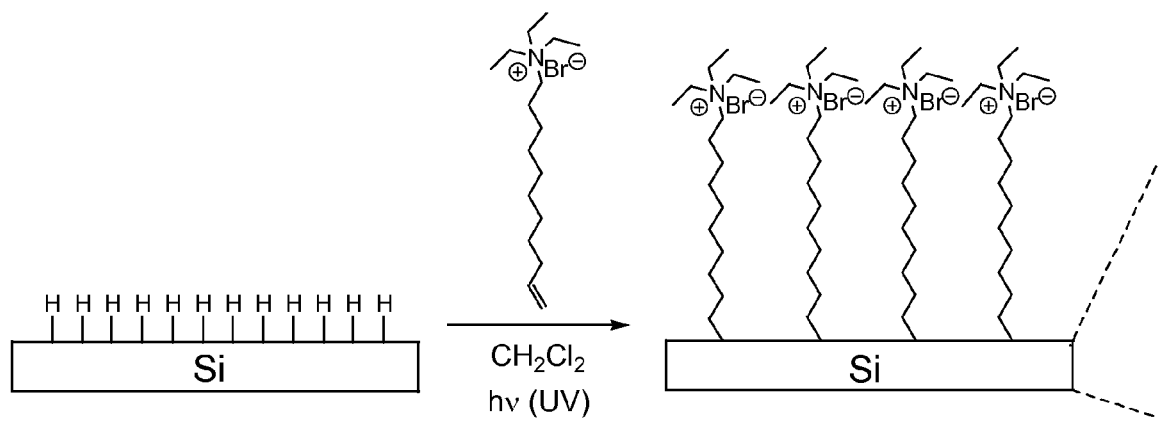
FIG. 8 shows photochemical hydrosilylation of 11-undecenyltriethylammonium bromide to hydrogen terminated microcantilevers.
Figure 9:
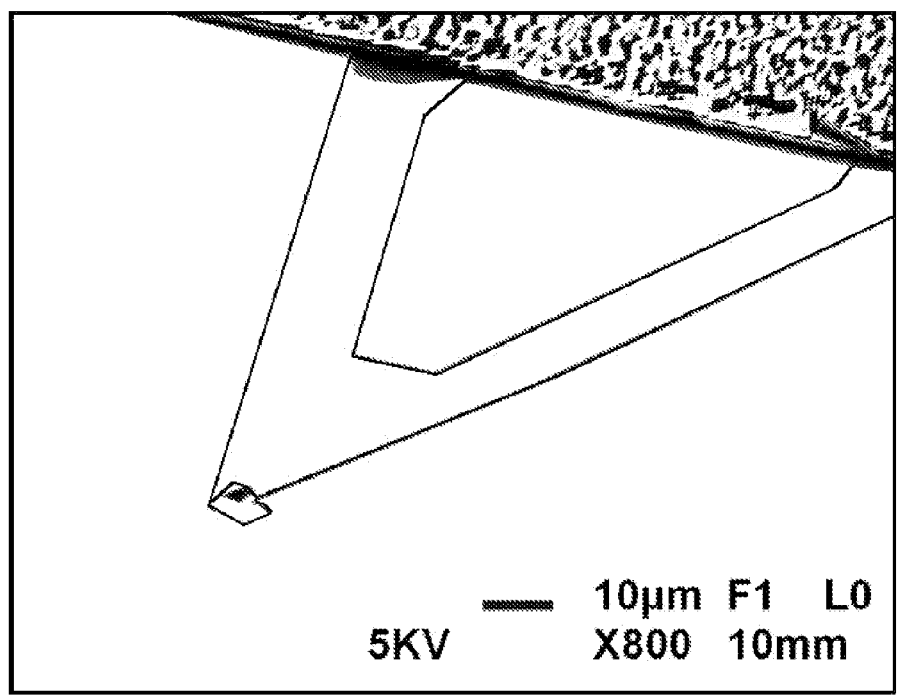
FIG. 9 is a photograph of a typical functionalized microcantilever.

Photochemical Hydrosilylation: Direct covalent attachment of the quaternary ammonium monolayer via robust Si—C bonds (FIG. 4) improved the stability and robustness of the cantilever sensors. This is achieved in a two-step process involving hydrogen termination of the silicon cantilever surface and subsequent photochemical (UV) hydrosilylation with the unsaturated hydrocarbon chain of the quaternary ammonium compound, which results in a stable Si—C surface linkage (FIG. 8).

11-Undecenyltriethylammonium bromide was synthesized in a one-step reaction by stirring 10 g (43 mmol) of 11-bromo-1-undecene (Aldrich Chemical Co., 95%) and 10 g (0.1 mol) of triethylamine (Aldrich, 99.5%) in absolute ethanol under argon for 24 h under reflux. Removal of the volatiles yielded a thick oil, which was triturated several times with ether to yield a white, hygroscopic solid (11.4 g, 80% yield) $C_{17}H_{36}NBr$ (MW=334.28). About 0.8 g of the white quaternary ammonium salt was then placed in a specially designed two-compartment quartz vacuum cell, dried and deoxygenated by prolonged evacuation until a base pressure of $2.1 \times 10^{-6}$ Torr was reached. Contact tipless V-shaped microcantilevers (180 μm long, 1 μm thick, and 25 μm wide, having a force constant of 0.26 N/m) from Thermomicroscopes, CA, were cleaned by the following procedure: soaking and washing in acetone (15 min), absolute ethanol (15 min), ultrapure (MilliQ) water, piranha (~10 s, 1:3 v 30% $H_2O_2$ and concentrated $H_2SO_4$), and ultrapure water and drying under argon flow. These cantilevers had been coated on one side with gold (a 30-nm thick gold layer on top of a 3-nm titanium adhesion layer) by the manufacturer. Hydrogen termination of the silicon surface was achieved by immersing each cantilever (~6 min) in 40% aqueous $NH_4F$ solution, which had been purged with argon for at least 30 min to remove dissolved oxygen. The resulting surface (Si—H) was dried in an argon flow and evacuated to remove any residual $NH_4F$. Each hydrogen-terminated silicon microcantilever was placed in a quartz tube (2 mm i.d.) and transferred under argon backflow into the second compartment of the quartz cell. Then all cantilevers were evacuated together with the quaternary ammonium salt. Anhydrous methylene chloride (Aldrich Chemical Co., 99.8%, bottled under nitrogen) was additionally dried with $CaH_2$, degassed by at least six freeze-pump-thaw cycles, and then distilled under vacuum into the cooled quartz cell compartment containing the 11-undecenyltriethylammonium bromide. Upon reaching room temperature, the quartz cell was backfilled with high-purity argon and a clear solution with an approximate concentration between 0.1 and 0.15 M was prepared under magnetic stirring. This solution was then carefully poured into the other cell compartment containing the hydrogen-terminated silicon microcantilevers. The argon-filled quartz cell was closed, disconnected from the vacuum manifold, and then placed into a bigger quartz vessel containing water to prevent heating during UV irradiation. The silicon surface was irradiated using frequencies emitted by a mercury lamp (100 W, ~25 cm distance from the surface) for 7-10 days to ensure sufficient time for dense packing of the positively charged quaternary ammonium terminated hydrocarbon chains. This time scale was prompted from our earlier results in the case of the self-assembly of mercapto-terminated quaternary ammonium hydrocarbon chains on gold-coated microcantilever surfaces, which needed about 1 week to yield the desired sensitivity to chromate ions. Following the photochemical reaction, the cantilevers were thoroughly rinsed with methylene chloride and water and then stored under ultrapure water until their response to chromate ions was measured. Blank tests performed on clean gold-coated silicon microcantilevers confirmed that unmodified cantilevers do not bend in response to $1 \times 10^{-4}$ M $CrO_4^{2-}$ nor do they respond even at concentrations as high as $1 \times 10^{-3}$ M, which is in agreement with our earlier reports. Control experiments show that no appreciable hydrosilylation takes place on the cantilever surfaces without UV irradiation at room temperature.

Cantilever deflection measurements were conducted in the optical mode using an atomic force microscopy (AFM) head. The experiments were performed in a flow-through glass fluid cell that holds the V-shaped microcantilever. The volume of the flow cell was 0.3 cm$^3$, ensuring fast replacement of the solution. A constant flow rate of 10 mL/h for the ultrapure (or tap) water carrier was maintained using a syringe pump. Samples of chromate solutions were introduced by directing the carrier through a 1-mL reservoir HPLC loop using a switch valve. This provided about 6 min contact time of the analyte with the active cantilever surface. The bending of the cantilever was measured by monitoring the position of a laser beam reflected off the apex of the cantilever (from the gold-coated surface) onto a position sensitive detector.

Using photochemically functionalized silicon microcantilevers, we were able to obtain significant bending response upon injection of $1 \times 10^{-4}$ M chromate solution in ultrapure water (FIG. 4, curve 1), a result which is in agreement with previous testing. In addition, as a result of the robust Si—C covalent linkage to the cantilever surface, the monolayer stability has been greatly improved. Well-defined signals were also registered at concentrations as low as $1 \times 10^{-9}$ M $CrO_4^{2-}$ in ultrapure water. This is also similar to the earlier results obtained using the Au-thiolate strategy for self-assembly of 12-mercaptododecyltriethylammonium bromide. This result illustrates that similar ultrahigh sensitivity of the microcantilever sensor to chromate ions can be achieved with a densely packed quaternary ammonium terminated monolayer derived from photochemical hydrosilylation directly on Si. Although there is no direct evidence for self-assembly, our data clearly indicate that the quaternary ammonium functionalities are readily accessible and packed closely enough to generate significant surface stress upon chromate adsorption. It is also clear (FIG. 4) that the cantilever deflection signal is quite readily reversible at the lowest concentrations of Cr (VI) (FIG. 4, curve 2), compared to the higher ($1 \times 10^{-4}$ M) concentration (FIG. 4, curve 1), although the latter case requires a longer time period (30 min).

Similar magnitude signals were registered upon injection of a $1 \times 10^{-4}$ M chromate solution in tap water, where tap water served as a background as well as a carrier fluid. It appears that washing with water recovers significant cantilever activity to new chromate loading. This effect has been discussed in greater detail earlier. In this study, tap or groundwater washing seems to regenerate cantilever activity faster compared to ultrapure water, most likely due to facilitated surface ion exchange. Signals with similar magnitude to that shown in FIG. 4, curve 1, were registered repeatedly using the same cantilever following multiple chromate injections and subsequent washing with ultrapure and tap water for a period of 11 days. This illustrates the expected stability of the functionalized silicon surface and low-level interference from the ions present in tap water with the chromate detection process under these experimental conditions. Another advantage of the stable quaternary ammonium cantilever sensor is its ability to detect chromate ions directly in liquid, neutral aqueous solutions, vapor, and gas, thus potentially eliminating the necessity for sample collection and preparation (such as acidifying to pH 1 in the case of the 4-mercaptopyridine based sensor). Such a chromate sensor that incorporates a reference cantilever (inert toward Cr(VI), for example, a clean Au-coated silicon cantilever) in a multicantilever array may be suitable for direct monitoring of groundwater and industrial wastewater. Using reference cantilever(s) in a multicantilever array can reduce adverse environmental effects such as gross changes in ionic strength and thermal drifts. Further optimization of this photochemical surface functionalization process may allow even better chromate sensitivity and selectivity with the desired stability and robustness necessary for field applications.

In the case of photochemical hydrosilylation, surface attachment of the quaternary ammonium terminated alkyl chains could occur via a radical-based mechanism proposed earlier, which involves homolytic Si—H bond cleavage giving rise to surface silicon radicals. Such silicon radicals react very rapidly with the unsaturated carbon-carbon bonds of 11-undecenyltriethylammonium bromide from the solution, thus restricting the radical chain reaction only to the surface. This model was strongly supported by the fact that no polymerization was observed in the solution during this photochemical reaction. The entire process can be limited by the access of the double-bond ends of the reactant to the activated surface, which becomes strongly hindered with increasing surface coverage. This is in addition to the electrostatic repulsion between the positively charged quaternary ammonium groups, which has appeared to significantly slow the self-assembly process of triethyl-12-mercaptododecylammonium bromide on gold surfaces (to about 1 week deposition time) compared to self-assembly of normal 1-thiols (a few hours to 1 day). Therefore, based on these earlier results, we have allowed sufficient time (6-10 days) in order to ensure dense packing of this particular ion-terminated organic layer, being fully aware that complete hydrosilylation of normal aliphatic alkenes such as 1-pentene and 1-octadecene on flat silicon surfaces has been reported to occur within only ~2 h. Indeed, long deposition time periods may not be such a serious issue for other types of organic layers, which do not contain ionic functionalities. In support of this argument, the best results in this study were obtained with cantilevers irradiated for 10 days.

In view of the long deposition time, thorough deoxygenation and dehydration of the quaternary ammonium salt and solvent were essential for this approach in order to avoid competitive oxidation of the hydrogen-terminated silicon surface under UV irradiation and to ensure effective surface functionalization. Only densely packed monolayers, functionalized with active head groups, can yield large surface stress upon analyte adsorption and thus a high sensitivity of detection. Once covalently attached to the silicon surface, the quaternary ammonium terminated hydrocarbon chains and the growing organic layer appears to be stable upon continued UV irradiation (for at least up to 10 days) under the conditions of our experiment. This is demonstrated by the magnitude of the response to chromate (FIG. 4, curve 1) following a period of prolonged irradiation.

Another embodiment of this invention is a method of modifying the surface of individual cantilevers in an array so that each cantilever (or a group of cantilevers) can have separate selectivity for sorption of analytes of interest. Furthermore the chemical modification involves the formation of robust Si—C bonds that are more chemically resistant than Si—O—Si bonding or the thiol SAMs on a gold coated microcantilever. Silicon microcantilevers having gold on one side are treated with $NH_4F$ to form Si—H terminated surface on the uncoated silicon side of the cantilever. This Si—H surface can be photochemically activated with UV light to react with an olefin. The olefin will not react with the Si—H bonds at room temperature, thus an array of cantilevers under a solution containing an olefin will not react until irradiated with UV light. To functionalize an array of cantilevers, the solution can be removed from the array of cantilevers, rinsed with a suitable solvent, and a second olefin functionalized with another molecular recognition end group can be added and induced to react with UV irradiation. This process can be repeated as often as necessary to create an array of cantilever sensors with different functionalities. This chemistry is compatible with a variety of molecular recognition agents including quaternary ammonium and pyridine groups (chromate selective), crown ethers and azacrown compounds (metal ion selective), borate esters (sugars), ureas (nitrate and organonitrate compounds), biomolecule-selective antibody-antigens, DNA, proteins, as well as organic acids, esters, amides, amines, aldehydes, phosphonic acids and esters, and related compounds.

For photochemical hydrosilylation, surface attachment of the quaternary ammonium terminated alkyl chains occurs via a radical-based mechanism summarized in Buriak, J. M. Chemical Reviews 2002, 102 (5), 1271-1308, herein incorporated by reference. This process involves homolytic Si—H bond cleavage giving rise to surface silicon radicals. Such silicon radicals react very rapidly with the unsaturated carbon-carbon bonds of alkenes dissolved in the solution, thus restricting the radical chain reaction only to the surface. This model was strongly supported by the fact that no polymerization was observed in the solution during this photochemical reaction. The entire process can be completed in as little as 2-3 hours or longer depending on desired functionality. The process can also be limited by the access of the double-bond ends of the reactant to the activated surface, which becomes strongly hindered with increasing surface coverage.

It is known in the organic and organometallic literature that UV irradiation can promote hydrosilylation of unsaturated compounds due to homolytic cleavage of Si—H bonds [Fleming, I. In Comprehensive Organic Chemistry; Jones, N., Ed.; Pergamon: New York, 1979; Vol. 3, p 568.] UV photoinduction takes place at room temperature and thus provides a way to avoid problems from thermal input that could be harmful to delicate or small features on a silicon chip. Minimal input of thermal energy would be preferable in any IC manufacturing process (thermal budget). Irradiation of a hydride-terminated Si (111) surface with UV light (185 and 253.7 nm) in the presence of an aliphatic alkene like 1-pentene or 1-octadecene brings about hydrosilylation in 2 h at room temperature, as shown in FIG. 5.

4-Mpy Functionalized Gold-coated Microcantilevers: The cantilever deflection measurements were conducted in the optical mode using an Atomic Force Microscopy (AFM) head. The cantilever bending signal (which depends on the cantilever dimensions as well as on the electronic circuit details) was converted to a surface stress in order to express in universal terms. The experiments were performed in a flow-through glass fluid cell that holds the V-shaped microcantilever (180 μm long, 1 μm thick, and a force constant of 0.26 N/m) from Thermomicroscopes, CA. The manufacturer had coated one side of these cantilevers with gold (a 30-nm thick gold layer on top of a 3-nm titanium adhesion layer). The metallic coating can be at least one of Au, Pt, Cu, Pd, Al, or Ti. The volume of the glass cell was 0.3 $cm^3$, ensuring fast replacement of the solution. A constant flow rate of 10 ml/hr for the acidic carrier solution (0.1 N $H_2SO_4$ in ultrahigh purity deionized water, pH 1) was used in these experiments; ground water samples or standard chromium (VI) solutions acidified the same way were injected into the carrier. The B-B stacking between the aromatic 4-mercaptopyridine (4-MPy) molecules and their conformational rigidity within the SAM have the tendency to align them into polymer-like chains, which can be observed by scanning tunneling microscopy (STM). These structures expose densely packed surface sites with high affinity for the chromate analyte, which is apparent from the selective chromate preconcentration. Ordered domains with pH-dependent row structure, where the fraction of protonated molecular rows depends on solution pH, have been observed on Au (111) modified by 4-MPy SAMs.

The earlier electrochemical studies of Turyan and Mandler together with the above STM studies and the high affinity of the pyridinium species towards chromate and dichromate ions (where pyridinium chlorochromate (PCC) is widely used as a mild oxidant) led to exploring this system for cantilever-based chromate sensors.

Gold-coated silicon cantilevers were cleaned in acetone, in absolute ethanol, in deionized water, and (for only 10 s) in piranha solution (7:3 $H_2SO_4$ 98%/$H_2O_2$ 31%), and rinsed with ultrapure deionized water (3 times) and absolute ethanol (2 times). The formation of a 4-MPy SAM on the gold surface of the cantilever was achieved by immersing the cantilever into an acidic aqueous solution of $5 \times 10^{-3}$ M of 4-MPy (95%, from Aldrich Chemical Company) in 0.1 N $H_2SO_4$/de-ionized water for six days. Upon removal from the solution, the cantilever was rinsed with de-ionized water and then dried before use in the experiments. Similar preliminary results were obtained with cantilevers modified using $\approx$5 mM 4-MPy in absolute ethanol. In both cases, large cantilever bending signals (corresponding to a cantilever stress of up to $\approx$1.3 N/m) were observed when de-ionized water was replaced by the acidified carrier due to SAM protonation.

Figures 1A, 1B:
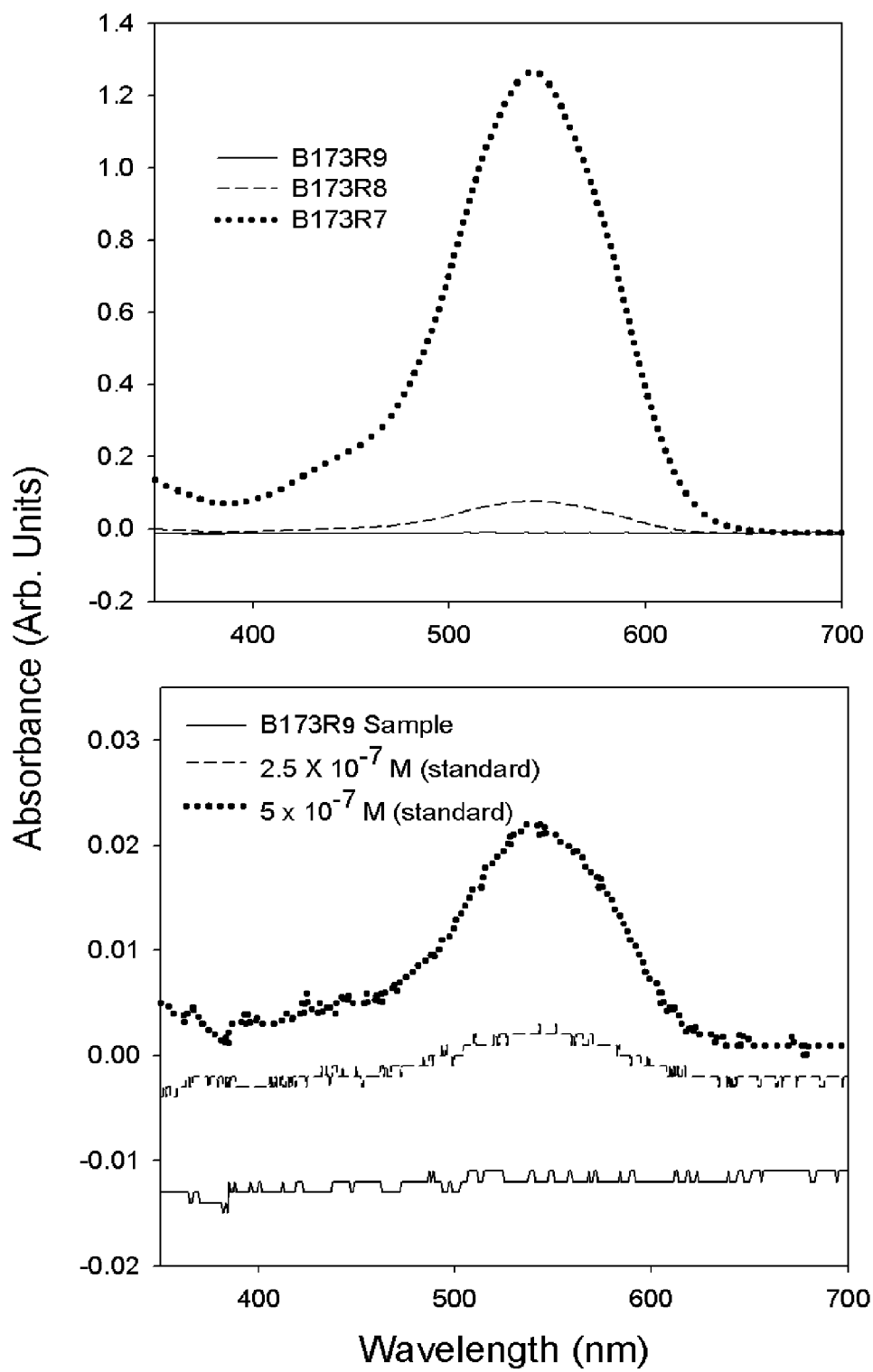
FIGS. 1a and 1b are graphs showing (a) Results of the photometric measurements on the three water samples from the Hanford site. (b) Comparison of the photometric signal from the B173R9 sample with those from standard chromate solutions of concentrations of $2.5 \times 10^{-7}$ M and $5.0 \times 10^{-7}$ M.

For comparison, photometric measurements were conducted on the ground water samples using a sample analytical kit that we purchased from the Hach company. FIG. 1$a$ shows the photometric data for the 3 samples. The chromate concentration in the B173R9 sample is below the detection level of the photometric method, and samples B173R8 and B173R7 have chromate concentrations of $\approx 2.4 \times 10^{-6}$ M and $\approx 3.7 \times 10^{-5}$ M, respectively. These numbers agree reasonably well with the historical data for these wells. We also measured the photometric signals due to standard chromate solutions of concentrations $5 \times 10^{-7}$ M and $2.5 \times 10^{-7}$ M and compared these with the signal due to the B173R9 sample; see FIG. 1$b$. It is quite clear that the chromate concentration in the B173R9 sample is well below $2.5 \times 10^{-7}$ M.

Figure 2A:
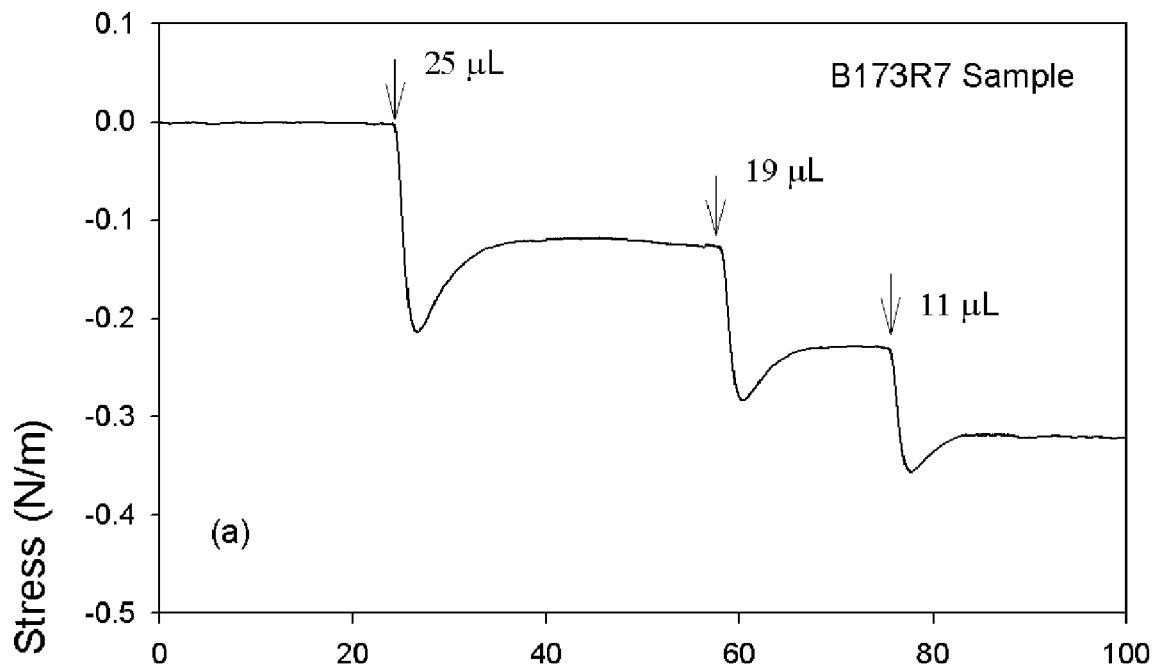
FIGS. 2a and 2b are graphs showing cantilever bending signals of 4-Mpy modified cantilever due to the injections of different amounts of the acidified sample solutions at 10 mL/hr; (a) different amounts of B173R7 and (b) same amount of B173R8 samples. The relative magnitudes of the cantilever bending signals (after normalizing to the injection volumes) are in agreement with the relative concentrations obtained from the photometric measurements.
Figure 2B:
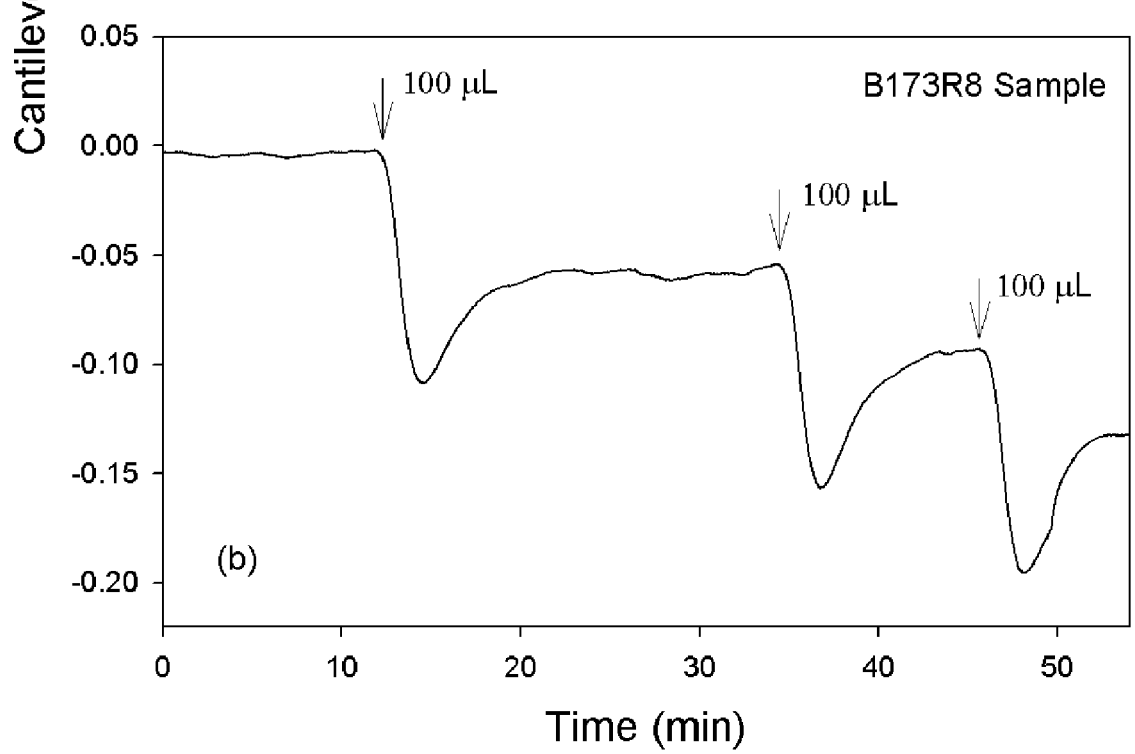

The cantilever bending response from acidified ground water samples B173R7 and B173R8 are shown in FIG. 2. As can be seen from FIG. 2($a$), the bending signal is roughly proportional to the amount of the sample injected; on the other hand, similar bending signals are obtained when the same amount of chromate is injected; see FIG. 2($b$). The signal level for the B173R8 sample is roughly 10 times smaller compared to that of the B173R7 sample when normalized to the injection volumes. Thus the cantilever bending data are in agreement with the photometric data for those two samples. In the data of FIG. 2 the cantilever bending is only partially recovered after the exposure to chromate. Even though this does not affect the reproducibility—we have done tens of injections—it is important to note that the cantilever bending can be quickly recovered back to the original state by electrocycling between 0.5 and −0.15 V at a rate of 50 mV/s in the acidic carrier. This procedure reduces Cr(VI) to Cr(III), which is repelled from the intact positively charged pyridinium SAM, thus clearing the surface for subsequent chromate adsorption. This procedure can be further simplified, optimized and incorporated into a low-cost cantilever-based analytical device to achieve the highly desired quick sensor recovery and fast multiple sample analysis.

Partially reversible chromate signals may be due to two-step surface process involving rapid reversible displacement of sulphate in the vicinity of the positively charged (protonated) 4-mercaptopyridinium layer for chromate (lower hydration energy), followed by stronger and much less reversible complexation, of chromate to the SAM surface. When the chromate sample is displaced from the flow cell by the carrier, fast (minutes) ion exchange in the diffuse ionic layer may be responsible for the fast initial recovery followed by much slower (hours) desorption of the strongly bound chromate.

The fast ion exchange of sulfate for chromate ions is, in general, not a selective process. There is a "bias" for large poorly hydrated anions over smaller hydrated anions. However, the slower complexation process should be chemically specific. There are very few anionic species like molybdate ($MoO_4^{2-}$), permanganate ($MnO_4^-$) and vanadate ($VO_4^-$), which can potentially react and interfere after the initial ion exchange step since their structure and size are similar to that of the chromate anion. Some cations like $Fe^{3+}$, $Ag^+$, $Cu^{2+}$ have also been shown to interfere at concentrations near and above $10^{4-}$M. In principle, most of these potentially interfering ions are quite toxic and if they ever reach the interfering level, their early detection in a routine field test would be as important as that of the chromate. From the detailed historical data of the ground wells used for sampling in this study, we could verify, that the concentration of any of the above potential interferences has always been at least 3 orders of magnitude below the interfering level reported by Turyan and Mandler. Therefore we do not anticipate any significant interference in our ground water measurements. As mentioned above, some small interference can be expected in the "fast reversible" ion exchange portion of the chromate bending signals from common mineral salts dissolved in the ground water samples. In our experiments this effect is strongly suppressed by the relatively high 0.1 N $H_2SO_4$ concentration in the carrier and acidified sample solutions. Small, usually less than mM concentrations of common mineral anions would not significantly displace the much more concentrated sulfate ions from the pyridinium surface layer. The high specificity of the pyridinium layer towards chromate justifies the use of acidified ultrapure water carrier to obtain a base-line for the chromate measurement. Preliminary evaluation of this common "ion exchange" interference effects was carried out by injecting acidified (0.1 N $H_2SO_4$) samples of commercially available Avian brand natural spring water ($Ca^{2+}$ 78 ppm, $Mg^{2+}$ 24 ppm, silica 14 ppm, $HCO_3^-$ 357 ppm, $SO_4^{2-}$ 10 ppm, $Cl^-$ 4 ppm, $NO_3^-$ 1 ppm) into the acidified (0.1 N $H_2SO_4$) ultra-pure water carrier. The bending signals were reversible and well within 0.03 N/m. As expected, their magnitude did not depend on the sample size and the contact time with the cantilever sensor. This is in contrast to the reference signals obtained from low concentration chromate samples (at and below $10^{-8}$ M $CrO_4^{2-}$), where the signal kept slowly increasing in magnitude as the sample size and the contact time with the cantilever sensor increased.

Complexation of chromate with pyridinium and pyridinium-terminated monolayers has been widely attributed to inter-ionic hydrogen bonding. In a very recent study, Mosier-Boss and Lieberman [*Langmuir* 19, 6826 (2003)] used a molecular modeling calculation to show the importance of the ordered pyridinium monolayer structure and proposed the existence of specific microcavities between adjacent pyridinium moieties on the SAM surface with a three-dimensional structure, complimentary in both shape and chemical functionality to that of the chromate ion. They have also discussed in detail, and supported with spectroscopic evidence, the different nature of interactions between pyridinium-terminated monolayers and $ClO_4^-$ (perchlorate ions, mainly electrostatic) as opposed to $CrO_4^{2-}$ (chromate, specific hydrogen bonding). The ion-pair constants calculated from the spectroscopically-obtained Frumkin isotherms indicate that the interaction of the pyridinium layer with $CrO_4^{2-}$ (specifically hydrogen bonding) is three orders of magnitude stronger than that for perchlorate (mainly electrostatic). This explains the high chromate selectivity and sensitivity. Furthermore, the negative value of the Frumkin parameter for the chromate-pyridinium interaction (g=−2.80±0.18) obtained in the study indicates a repulsive force between the adsorbed chromate ions, which becomes very significant at high surface concentrations. These repulsive chromate-chromate interactions may be responsible for the extremely large cantilever bending signals (>1 N/m) at high chromate surface coverage, reflecting a huge increase of the adsorption-induced surface stress. In light of this argument, it is important to note that the cantilever sensitivity significantly increased after a "critical" surface concentration of pre-adsorbed chromate was achieved by injection of standard chromate solution (following the electrochemical recovery). It apparently remains steady until high chromate coverage (near 1 N/m of total cantilever bending signal and higher) is achieved. The data shown in this work are taken within this sensitivity range. In a real device the sensitivity can be periodically verified and corrected by injection of small volume low-concentration chromate standard to determine the exact sensitivity factor for the following and previous sets of samples. Overloading of the cantilever sensor can be prevented by using small sample volumes and short contact times at high chromate concentrations as seen in FIG. 2. If overloaded, the cantilever sensor can be quickly recovered electrochemically as described above. It was also found that following a number (>10) of chromate injections (significant chromate loads), prolonged wash (overnight) with acidified ultrapure water (~60 ml at slow pumping speeds of few ml/hr) recovers the cantilever sensor capacity within the working sensitivity range as during the previous day and thus, no pre-adsorption of chromate was necessary in order to obtain high intensity bending signals with magnitude similar to that of the corresponding samples analyzed during the previous day. This can be attributed to the slow desorption of the "overstressing" hydrogen-bonded chromate surface species facilitated by the repulsive chromate-chromate interactions at high surface coverage, as well as by the elastic forces of the strongly bent cantilever and the concentration gradient. The remaining chromate species will have a low enough surface density, which assures minimal chromate-chromate electrostatic repulsion. The sensor is than ready to respond with a strong signal to any, even minimal, change in the surface stress induced by adsorbing any chromate ions in closer than this equilibrium proximity. The mobile nature of any hydrogen-bonding interaction, leads to the removal of pre-adsorbed chromate species by the clean acidified water carrier.

Cantilever response to the acidified B173R9 sample (FIG. 3) shows that the cantilever is able to detect this low chromate level clearly. Comparing this signal magnitude with cantilever data for the B173R7 sample (FIG. 2($a$)) and the B173R8 sample (FIG. 2($b$)) yielded estimated concentrations of $1\times10^{-7}$ M and $6\times10^{-8}$ M respectively for the B173R9 sample. Therefore, we estimate the concentration of the B173R9 sample to be $\approx 8\times10^{-8}$ M. At lower chromate concentrations, much larger sample volumes are used at the same pumping speed, thus also increasing the contact time between the chromate and the pyridinium layer.

Figure 3:
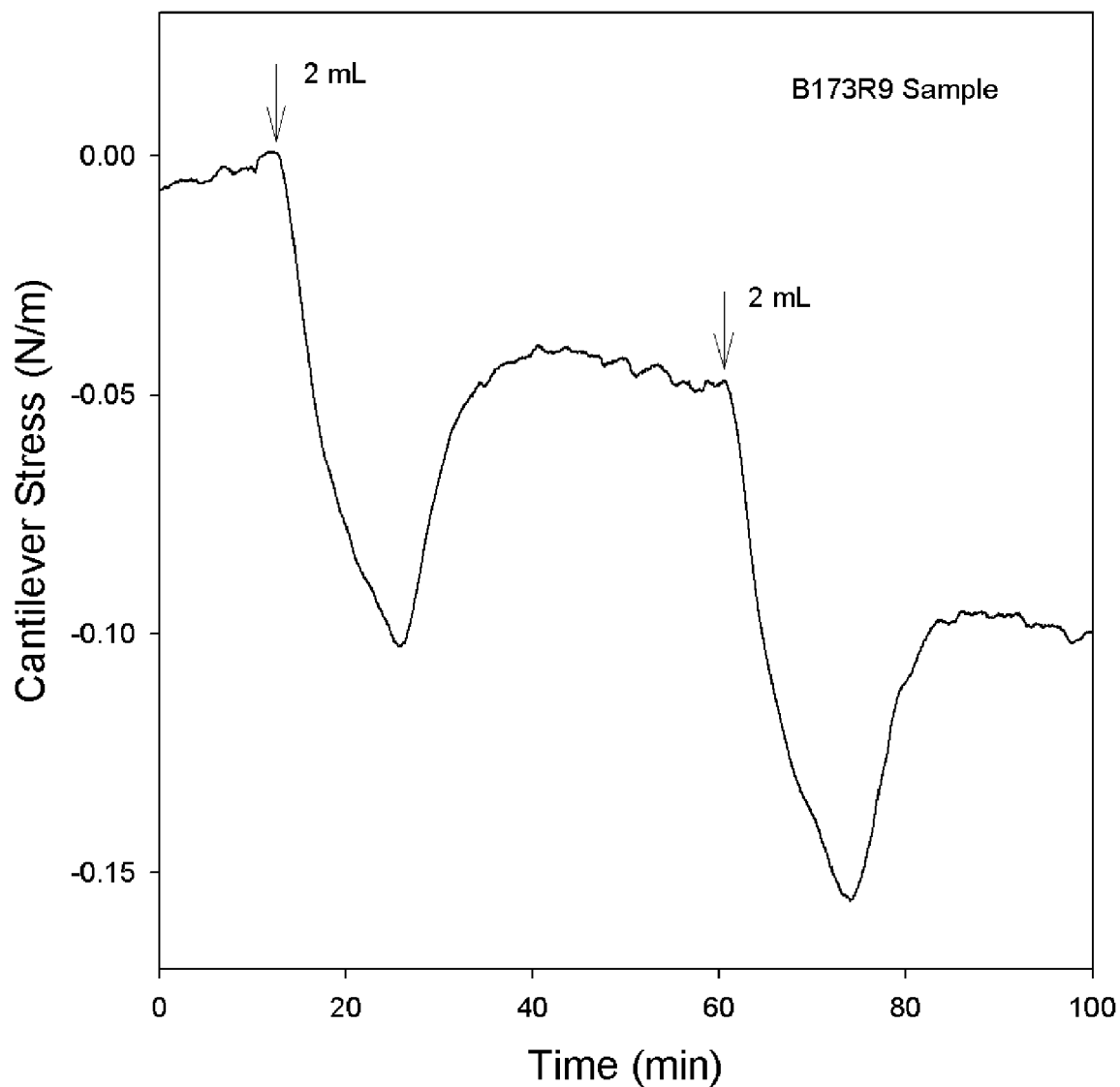
FIG. 3 is a graph showing cantilever bending signal due to the injection of 2 mL (at pumping speed of 10 mL/hr) of the acidified B173R9 water sample taken from a well at the Hanford site. From historical data for this well, the concentration of hexavalent chromium is expected to be $<2.5 \times 10^{-7}$ M. The water from this well contains numerous other contaminants, some of which have concentrations exceeding $10^{-4}$ M.

An estimate of the detection threshold can be obtained by using the data of FIG. 3, and estimating the chromate concentration that would be above the noise level of FIG. 3. By taking the noise level to be 3 standard deviations of the background fluctuations (i.e. $\approx 3\times0.002$ N/m), we obtained a detection threshold of $4\times10^{-9}$ M. When we injected standard chromate solutions of varying concentrations made out of calibrated acidic chromate samples, we were able to observe clear signals above/near $1\times10^{-8}$ M. Therefore, the detection threshold is roughly an order of magnitude better than the photometric method. It may be possible to improve the sensitivity further by varying the pH, contact time with the chromate sample, and SAM quality, as well as the cantilever specific parameters and substrate cleaning procedure; such studies are underway in our laboratory. Furthermore, we have used a few cantilevers with the 4-mercaptopyridine coating for several months without any apparent decrease in performance.

Further details are discussed in the following literature, herein incorporated by reference:
1) Terry, J.; Linford, M. R.; Wigren, C.; Cao, R.; Pianetta, P.; Chidsey, C. E. D. *Appl. Phys. Letter.* 1997, 71, 1056-1058.
2) Terry, J.; Mo, R.; Wigren, C.; Cao, R.; Mount, G.; Pianetta, P.; Linford, M. R.; Chidsey, C. E. D. *Nucl. Instrum. Methods Phys. Res.*, Sect. B 1997, 133, 94.
3) Terry, J.; Linford, M. R.; Wigren, C.; Cao, R.; Pianetta, P.; Chidsey, C. E. D. *J. Appl. Phys.* 1999, 85, 213.
4) Cicero, R. L.; Linford, M. R.; Chidsey, C. E. D. *Langmuir,* 2000, 16, 5688.
5) L. A. Pinnaduwage V. I. Boiadjiev, G. M. Brown, T. Thundat, S. W. Petersen, "Detection of Hexavalent Chromium in Ground Water Using a Single Microcantilever Sensor", *Sensor Letters* Vol. 2, No. 1 (2004).
6) V. I. Boiadjiev, G. M. Brown, L. A. Pinnaduwage, G. Goretzki, P. V. Bonnesen, and T. Thundat, "Photochemical Hydrosilylation of 11-Undecenyltriethylammonium Bromide with Hydrogen-Terminated Si Surfaces for the Development of Robust Microcantilever Sensors for Cr(VI)", *Langmuir,* ASAP Article 10.1021/la047852n S0743-7463(04)07852-7; Web Release Date: Jan. 20, 2005.
7) X. Zhou, M. Ishida, A. Imanisahi, Y. Nakota, "Roles of Charge Polarization and Steric Hindrance in Determining the Chemical Reactivity of Surface Si—H and Si—Si Bonds at H-Terminated Si(100) and -(111)", *J. Phys. Chem. B,* 2001, 105, pp 156-163.
8) A. Arafat, K. Schroen, L. C. P. M. de Smet, E. J. R. Sudholter, H. Zuilhof, "Tailor-Made Functionalization of Silicon Nitride Surfaces", *J. Am. Chem. Soc.,* 2004, 126, pp 8600-8601.
9) R. Voicu, R. Boukherroub, V. Bartzoka, T. Ward, J. T. C. Wojtyk, D. D. M. Wayner, "Formation, Characterization, and Chemisty of Undecanoic Acid-Terminated Silicon Surfaces: Patterning and Immobilization of DNA", *Langmuir,* 2004, 20, pp. 11713-11720.
10) C. M. Yam, J. M. Lopez-Romero, J. Gu, C. Cai, "Protein-resistant Monolayers Prepared by Hydrosilylation of α-Oligo (ethylene glycol)-ω-Alkenes on Hydrogen-Terminated Silicon (111) Surfaces", *Chemical Communications,* 2004, pp. 2510-2511.

A range of alkenes and alkynes were successfully tried, including 1-octene, 1-octadecene, 1-octyne, styrene, and phenylacetylene, with the alkenes yielding alkyl monolayers and the alkynes yielding alkenyl monolayers. Examples of surfaces prepared and discussed in the literature are shown in FIG. 6.

Figure 7:
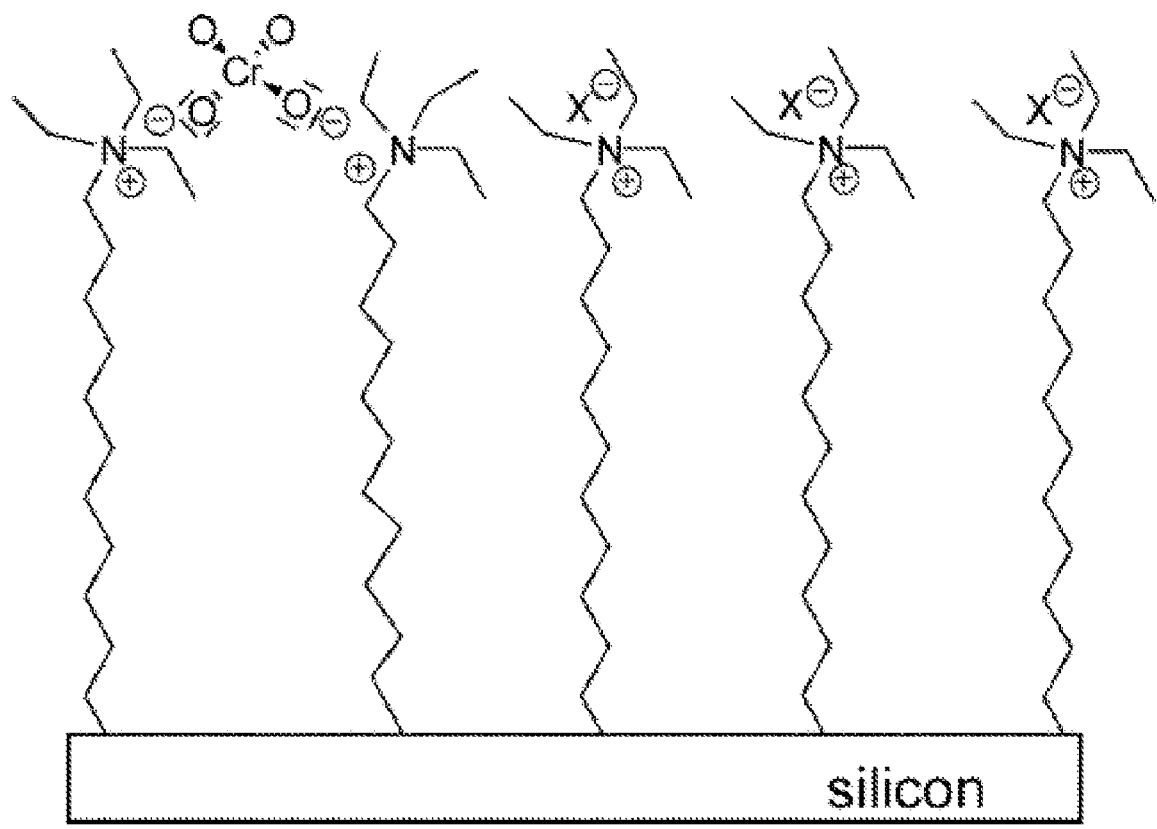
FIG. 7 shows anticipated structure of Si surface modified with quaternary ammonium coating and bonding mode for chromate. It is a schematic representation of a cantilever Si surface functionalized with 11-undecenyltriethylammonium halide using the photochemical hydrosilylation approach for chromate detection. X—=Br— immediately following the hydrosilylation process.

According to Buriak, the mechanism proposed is radical based, with homolytic Si—H bond cleavage initiating the reaction to form a silicon radical (dangling bond). Because silicon radicals are known to react very rapidly with unsaturated carbon-carbon bonds, Si—C bond formation is expected to be a facile step, forming the surface-bound carbon-based radical on the ω-carbon of the olefin. Abstraction of neighboring hydrogen completes the hydrosilylation. On the basis of the bond strengths of the weakest Si—H bond on a silicon surface, the monohydride Si—H group (~3.5 eV), it appears that a minimum of 3.5 eV UV (<350 nm) is required to efficiently perform Si—H bond homolysis. Buriak reports that irradiation of the Si(111)—H surface in air results in fast and efficient loss of hydrides, as observed by ATR-FTIR, only at wavelengths shorter than 350 nm, again pointing to the threshold near this wavelength for Si—H bond activation on this surface As an example we attached a quaternary ammonium group to the surface of a cantilever and demonstrated that we could use this modified cantilever to sense Cr(VI) in solution. A long reaction time was chosen because of the electrostatic repulsion between the positively charged quaternary ammonium groups, which has appeared to significantly slow down the self assembly process of triethyl-12-mercaptododecylammonium bromide on gold surfaces (to about one week deposition time) compared to self-assembly of normal 1-thiols (few hours to 1 day). Therefore, based on these earlier results, we have allowed sufficient time (6 to 10 days) in order to assure dense packing of this particular ion-terminated organic layer, being fully aware that complete hydrosilylation of normal aliphatic alkenes like 1-pentene and 1-octadecene on flat silicon surfaces has been reported to occur within only ~2 hrs. Indeed, long deposition time periods may not be such a serious issue for other types of organic layers, which do not contain ionic functionalities. In support of this argument, best results in this study were obtained with cantilevers irradiated for 10 days. The proposed surface structure is shown in FIG. 7.

The photochemical surface activation strategy can also allow individual cantilevers in multicantilever array chips to be modified separately by focusing the activating UV light sequentially on each particular cantilever. A set of reactant solutions can be prepared and recycled in a sequential photochemical treatment procedure where the array will be exposed to one solution at a time. The entire chip would be washed with solvent following each UV irradiation before the next solution is brought in. This will allow specific modification of individual irradiated cantilevers on the chip, which cannot be achieved using non-selective thermal activation. Thermal activation would initiate deposition of the same organic layer on all cantilever surfaces at the same time. In addition, carrying out the photochemical reaction at ambient temperature eliminates cantilever deformations due to bimetallic effects upon heating. Increasing the number of independently functionalized cantilevers on an array chip would strongly enhance the recognition power of the sensor device. Such modified surfaces can also be used as reactive platforms for further surface functionalization by spotting.

The Ti/Au coating of the cantilevers did not appear to interfere with the photochemical silicon functionalization process when a 40% NH4F solution was used to produce the hydrogen-terminated silicon surface. It was severely attacked when an HF treatment was attempted. Nevertheless, a protective Ti/Au coating may not be required if only one side of the lever can be selectively modified during the photochemical hydrosilylation step, while the other hydrogen-terminated silicon side will oxidize back to its original functionality upon contact with water and air following the photochemical process.

Photochemical hydrosilylation of silicon cantilevers is suitable for cantilever sensor development if the desired surface functionality is compatible with the reaction requirements. The resulting functionalized organic layers can be dense enough to generate sufficient surface stress upon specific analyte adsorption at low concentrations. Cantilever sensors prepared using these strategies have unsurpassed robustness and stability due to the direct covalent Si—C linkage.

Although the single cantilever approach seems to work extremely well in laboratory applications, it is less useful in real environment applications where many other parameters can produce signal interference. To avoid this potential problem, it is necessary to look at the differential response of a set, or array, of cantilevers. For example, variations in physical parameters such as temperature, acceleration, and mechanical noises can contribute to cantilever bending. Differential signals obtained by common mode rejection can provide highly sensitive data.

Chemical selectivity can be achieved by arrays consisting of several microcantilevers, each coated with different selective or partially selective coatings. The response of a given modified microcantilever will depend on the concentration of the analyte and the strength of the coating-analyte interactions (e.g. hydrogen bonding, dispersion, and dipole-dipole interactions). A unique response pattern characteristic to a particular analyte can be obtained from an array where each microcantilever is modified with a different coating. The higher the number of modified cantilevers, the greater the uniqueness of the response pattern. Since the microcantilever response to a given analyte depends on the functional end-groups of modifying agents, judicious selection of coatings can lead to significant differences in the response patterns for different analytes. Using an array consisting of a large number of microcantilevers, unique response patterns can be attained for individual analytes, class of analytes, or analytes in complex mixtures. The results of testing with a large number of analyte and mixtures are recorded in a look-up table and referenced routinely when an array is in service.

Using hydrosilylation procedure, which in certain cases can be combined with sequential surface reactions, it is possible to derive coatings containing various molecular recognition groups such as hydrocarbon chains, esters, metal-containing organic functionalities, buckyballs (C-60), carboxylic acids, and even hydroxyls. One example is the use of hydrocarbon layers grafted directly on the silicon surface for gasoline detection (FIG. 6). Environmental sampling and process control are areas wherein the arrays offer advantages of size, simplicity and reliability.

While there has been shown and described what are at present considered the preferred embodiments of the invention, it will be obvious to those skilled in the art that various changes and modifications can be made therein without departing from the scope.

We claim:

1. A method for providing a plurality of molecular recognition agents on an individual semiconductor device having a plurality of microcantilevers, each microcantilever having a silicon surface on one side and a metal-coated surface on another side, the method comprising:
    a. cleaning said silicon surface of said at least one microcantilever,
    b. hydrogen terminating said silicon surface on said at least one microcantilever silicon surface,
    c. carbon linking a first molecular recognition agent to the hydrogen terminated silicon surface of said at least one microcantilever using photochemical hydrosilylation,
    d. immersing said hydrogen terminated silicon surface in a molecular recognition agent solution
    e. irradiating said hydrogen terminated silicon surface with ultraviolet light to activate said microcantilever for recognition of a selected molecule;
    f. rinsing said hydrogen terminated silicon surface; and
    g. repeating steps a. thru f. for a plurality of different molecular recognition agents that are associated with respective different individual cantilevers.

2. The method of claim 1, wherein said cleaning step further comprises the sequential steps of:
   a. rinsing in acetone,
   b. rinsing in absolute ethanol,
   c. rinsing in deionized water,
   d. rinsing in piranha solution,
   e. rinsing in ultrapure deionized water, and
   f. rinsing in absolute ethanol.

3. The method of claim 1, wherein said hydrogen terminating step further comprises:
   a. immersing said silicon surface in approximately 40% $NH_4F$ argon-purged solution, and
   b. drying said silicon surface in argon.

4. The method of claim 1, wherein said first molecular recognition agent consists of an olefin.

5. The method of claim 1, wherein said different molecular recognition agents further comprise agents selected from the group consisting of quaternary ammonias, crown ethers, aza-crown compounds, borate esters, ureas, biomolecule-selective antibody-antigens, DNA, proteins, organic acids, organic esters, organic amides, organic amines, organic aldehydes, phosphonic acids, phosphonic esters, buckyballs, and hydroxyls.

6. The method of claim 4, wherein said first molecular recognition agent further comprises 11-undecenyltriethylammonium bromide.

7. The method of claim 1, wherein said ultraviolet light is emitted from at least one of a mercury lamp and a laser.

* * * * *